United States Patent [19]

Gerlock et al.

[11] 4,336,406

[45] Jun. 22, 1982

[54] POLYOL EXTRACTION BY HIGH BOILING ALKANES

[75] Inventors: John L. Gerlock, Dearborn; Jacob Braslaw, Southfield, both of Mich.; William E. Stevens, Long Valley, N.J.

[73] Assignee: Ford Motor Company, Dearborn, Mich.

[21] Appl. No.: 237,568

[22] Filed: Feb. 24, 1981

[51] Int. Cl.$^3$ .............................................. C07C 41/01
[52] U.S. Cl. ..................................... 568/621; 568/613
[58] Field of Search .................. 568/621, 613; 260/2.3

[56] References Cited

U.S. PATENT DOCUMENTS

| | | |
|---|---|---|
| 2,973,151 | 5/1960 | Broeck et al. . |
| 3,109,824 | 11/1963 | Heiss . |
| 3,117,940 | 1/1964 | McElroy . |
| 3,123,577 | 3/1964 | Heiss . |
| 3,300,417 | 1/1967 | McElroy . |
| 3,404,103 | 10/1968 | Matsudaira et al. . |
| 3,441,616 | 4/1969 | Pizzini et al. . |
| 3,632,530 | 1/1972 | Kinoshita . |
| 3,708,440 | 1/1973 | Frulla et al. . |
| 3,738,946 | 6/1973 | Frulla et al. . |
| 3,954,681 | 5/1976 | Castle . |
| 3,983,087 | 9/1976 | Tucker et al. . |
| 4,014,809 | 3/1977 | Kondo et al. . |
| 4,035,314 | 7/1977 | Lohr, Jr. et al. . |
| 4,039,568 | 8/1977 | Sakai et al. . |
| 4,110,266 | 8/1978 | Sheratte . |
| 4,115,298 | 9/1978 | Schneider et al. . |
| 4,159,972 | 7/1979 | Braslaw et al. . |
| 4,162,995 | 7/1979 | Sheratte . |

FOREIGN PATENT DOCUMENTS

| | | |
|---|---|---|
| 1110405 | 7/1961 | Fed. Rep. of Germany ....... 260/2.3 |
| 2738572 | 3/1979 | Fed. Rep. of Germany . |

*Primary Examiner*—Howard T. Mars
*Attorney, Agent, or Firm*—Lorraine S. Melotik; Roger L. May

[57] ABSTRACT

Polyol is recovered from polyurethane based polyurethane foam by a process which includes first dissolving the foam in a saturated alcohol, preferably diethylene glycol, having a boiling point between about 225° C. and 280° C. at a temperature between about 185° C. and 220° C. under a non-oxidizing atmosphere. The solution is reacted with water in the presence of an alkali hydroxide catalyst, preferably sodium hydroxide, under a non-oxidizing atmosphere, such as nitrogen. This may be done by refluxing the solution at a temperature between about 175° C. and 220° C. until all the carbamates produced during dissolution have been hydrolyzed to amines and alcohol. Water remaining in solution after hydrolysis is removed. A high boiling alkane is used to extract the polyol from the solution still under a non-oxidizing atmosphere and then the extracted polyol is subjected to vacuum purification at a temperature of less than about 230° C. Substantially pure polyol is recovered which can be used to make new foam.

25 Claims, 3 Drawing Figures ered waste generates over 50 million pounds of low
POLYOL EXTRACTION BY HIGH BOILING ALKANES This invention relates to the recovery of polyol from polyurethane foam, which polyol can subsequently be used to produce high quality new foam. More particularly, this invention relates to a process which includes first reacting the polyether based polyurethane foam with a saturated alcohol, and then hydrolyzing the mixture in the presence of water and catalyst. A high boiling alkane is then used to extract the polyol from the solution, which polyol is recovered in substantially pure form.

RELATED APPLICATIONS

Reference is made to commonly assigned related U.S. applications Ser. No. 237,027 to Gerlock et al. filed Feb. 23, 1981 and entitled "Process for Polyol Recovery from Polyurethane Foam Comprising Alcohol and Steam Hydrolysis" and Ser. No. 237,008 to Gerlock et al. filed Feb. 23, 1981 entitled "Catalyzed Dissolution-Hydrolysis of Polyurethane Wastes".

BACKGROUND OF THE INVENTION

Currently, it is estimated that manufacturing associated waste generates over 50 million pounds of low density polyurethane foam each year. This form is generally disposed of in land-fill operations. Because of the economic loss associated with both the land required for land-fill and the foam disposed of in these operations, it is highly desirable to utilize the scrap foam or its chemical components in new product manufacture. One such chemical component which can be recovered from the scrap foam, and which is of particular commercial interest, is polyol, which can be used to manufacture new foam.

Prior art polyol recovery processes have included dissolving the foam and subsequently using the resulting solution without further purification to make new foam. In German Pat. No. 2,738,572, polyurethane wastes are heated in a diol containing a basic catalyst to prepare a homogenous polyol component to be used in the production of new foam. U.S. Pat. No. 2,937,151 to Broeck et al teaches dissolving scrap foam in high molecular weight polyesters, polyester amides or polyalkylene ether glycols, similar to those used to make the foam; the resulting solution is then crosslinked with isocyanate to generate new foam. Heiss, in U.S. Pat. No. 3,123,577, mills cellular polyurethane plastic, dissolves the particules in a high molecular weight trihydric polyalkylene ether containing a tin catalyst, and reacts the resulting resin with polyisocyanate to form new cellular polyether polyurethane. Tucker et al, in U.S. Pat. No. 3,983,087, heat scrap foam in a glycol wherein the alkylene chain separating the hydroxyl groups is branched. This homogeneous mixture can be used to make new foam. Braslaw et al, in U.S. Pat. No. 4,159,972, dissolve the foam in a low molecular weight diol, admix a high molecular weight polyol therewith, remove the diol under vacuum and use this product to make new foam. Kinoshita, in U.S. Pat. No. 3,632,530 heat the foam in a glycol and an amino compound in the presence of a tertiary amine catalyst. Upon standing, the mixture separates into a glycol containing amine layer and a layer comprising polyalkylene ether polyol. The polyol layer is used to produce new foam. Frulla et al., in U.S. Pat. No. 3,738,946 heat scrap foam in an aliphatic diol, preferably in the presence of a dialkanolamine. The resulting material is used without further purification to make new foam. U.S. Pat. No. 3,708,440 to Frulla et al is similar, employing an aliphatic diol and a dialkanolamine. McElroy, in U.S. Pat. No. 3,300,417, liquifies a polyurethane plastic by heating the polyurethane in an organic liquid in the presence of a metal catalyst, preferably a tin compound. The resulting liquid is reacted with a polyisocyanate to prepare a new cellular polyether polyurethane.

Hydrolysis has also been used on polyurethane foam to recover polyol. Lohr, in U.S. Pat. No. 4,035,314, hydrolyzes foam using superheated steam, dissolves the resulting oily residue in solvent, and further treats this mixture by a process comprising gassing with hydrochloric acid gas and ultimately recovering polyol. Pizzini et al, in U.S. Pat. No. 3,441,616, hydrolyze a polyether polyurethane foam with a strong base in a dimethylsulfoxide-water medium, extract the resulting polyol with a hydrocarbon solvent immiscible with the hydrolysis medium, separate the polyol solvent layer and strip off the solvent to recover polyol.

In spite of the numerous known processes for scrap foam utilization and polyol recovery, however, scrap foam is still generally disposed of in land-fill operations, indicating that none of these polyol recovery processes is commerically feasible. Therefore, a commercially feasible process for high grade polyol recovery has continued to be the subject of research.

An object of the subject invention is the recovery from scrap or waste polyether polyurethane foam of substantially pure polyether polyols, which, unlike prior art recovered polyol, are physically and chemically indistinguishable from the virgin polyol used to make the original foam, and may then be used to produce a high quality flexible foam of high resilience.

A further object of the invention is the processing of the foam in a commercially economical and rapid manner.

BRIEF DESCRIPTION OF THE INVENTION

It has been found that substantially pure polyether polyol can be readily recovered from polyether polyurethane waste foam by a process which includes first dissolving the foam in a saturated alcohol at a temperature between about 185° C. and 220° C. under a non-oxidizing atmosphere. The alcohol has a boiling point of between about 225° C. and 280° C.

The solution is reacted with water, in the presence of an alkali metal hydroxide catalyst for a time necessary to substantially hydrolyze dissolution productions subject to hydrolysis into amines and alcohol while maintaining a temperature of between about 175° C. and 220° C., under a non-oxidizing atmosphere. The water is included in the solution in an amount sufficient to create an mixture which has a boiling point within the temperature range of from about 175° C. to about 220° C. The alkali metal hydroxide catalyst is included in the solution in an amount of at least about 0.1 weight percent based on the weight of said foam. After hydrolysis, water remaining in solution is removed. The polyol is then extracted from the solution with an alkane substantially immiscible with said alcohol and having a boiling point between about 230° C. and about 300° C. The extracted polyol is subjected to vacuum purification at a temperature below about 230° C. to allow recovery therefrom of substantially pure polyol.

In the process of this invention by substantially pure polyol is meant that the recovered polyol is substantially free of recovery process by-products which reduce the quality of the new foam generated from the recovered polyol and thus limit the amount of recovered polyol that can be used to replace virgin polyol in a new foam production. Furthermore, it is meant to discribe a polyol which may be used to replace virgin polyol in substantial amounts in new foam production and yields a polyurethane foam with similar properties to the foam made with all virgin polyol.

DETAILED DESCRIPTION OF THE INVENTION

Typical low density polyurethane foams which can be processed by means of this invention are formed by reacting difunctional isocyanates with water, excess difunctional isocyanates and polyether triols. The polyurethane structure consists essentially of polyurea chains crosslinked with the triols by means of urethane linkages. In some foams, this structure is modified and further crosslinked by the presence of allophanate linkages which may occur when additional excess isocyanates are introduced. The preparation of the foam may also include catalysts, surfactants, fillers and other modifiers including amines in minor amounts. In addition to flexible foam, semi-flexible and rigid foams can also be utilized in the recovery process of this invention.

The polyether polyurethane foams which can be processed by the method of this invention, however, are not limited to those produced as described above.

The initial step of the invention comprises reacting the foam with a saturated alcohol, wherein the hydroxy functionality of the alcohol causes dissolution of the polyurethane, forming dissolution products which comprise polyol, ureas and carbamates. Any saturated alcohol with a boiling point between about 225° C. and 280° C. can be used. The alcohol can contain single or multiple hydroxy functionality and it can be straight chain, branched, cyclic or aromatic. Low molecular weight diols such as diethylene glycol, dipropylene glycol, dibutylene glycol, glycerol, or even polyether triols are preferred solvents. However, diethylene glycol is particularly preferred for reasons including availability and relatively low cost. Additionally, it is conveniently removed under vacuum from the recovered polyol at temperatures below about 230° C., thereby preventing discoloration and degradation of the polyol that can occur at higher temperatures.

Figure 1:
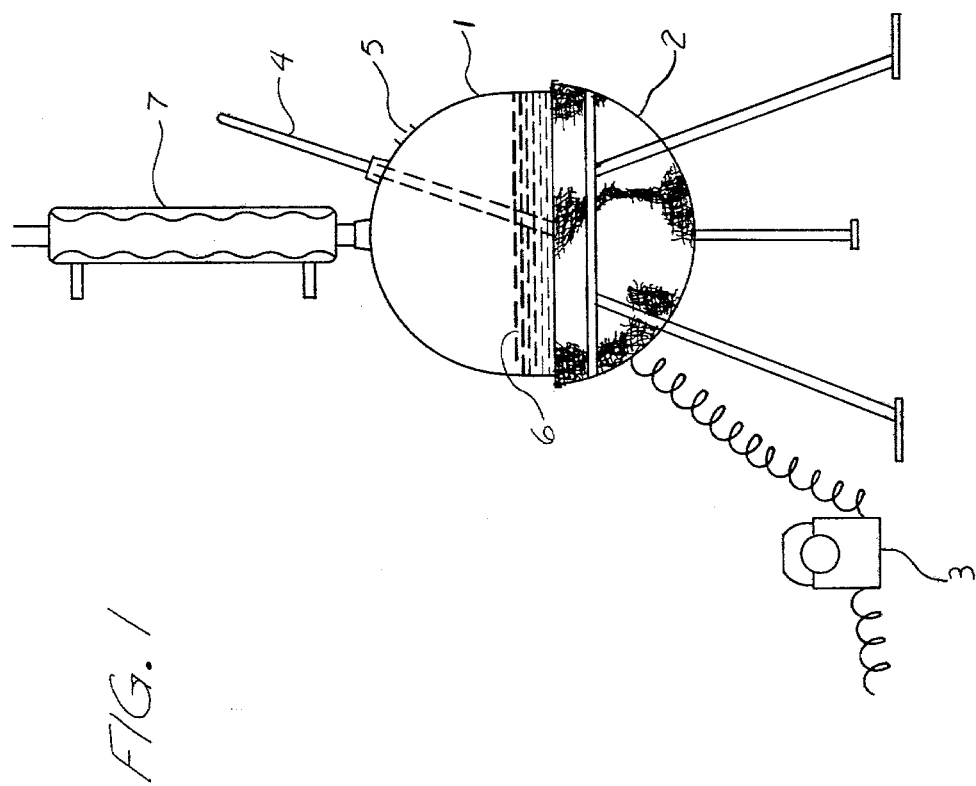
FIG. 1 shows a typical laboratory apparatus set-up which could be used in the process of the subject invention.

After first preheating the alcohol to between about 185° C. and 220° C., preferably about 200° C., with constant stirring, pieces of polyurethane foam are added until dissolution occurs, after which more pieces of foam are added. The process of the invention is carried out in a non-oxidizing atmosphere. As used herein "non-oxidizing atmosphere" means any atmosphere that excludes oxygen and does not lead to the formation of undesirable side reaction products, i.e. any polyol side reaction products or other side reaction products that may interfere with isolation of polyol from other reaction products. Suitable non-ozidizing atmospheres which can be provided are, for example, nitrogen, carbon dioxide, steam or the inert gases. A conventional laboratory set-up, as shown in FIG. 1 can be used in the process of this invention. The solution 6 is heated in a reactor 1 under a non-oxidizing atmosphere such as nitrogen which enters the reactor through 5. A conventional heating unit 2 is controlled by thermostat 3. The temperature of the solution is indicated by thermometer 4 immersed in the solution. A conventional stirrer (not illustrated) is used.

The amount of polyurethane foam that may be dissolved in the alcohol is limited only by the viscosity of the resulting solution, the more dissolved, the higher the viscosity. The ratio by weight of foam which can be dissolved, for example in diethylene glycol is between about 1:5 and 2:1, the preferred ratio being between 1:1.5 and 1.5:1. Most preferably, the weight ratio of foam to alcohol is 1:1. Using this process with rapid mixing, it takes less than one hour to dissolve 70 grams of foam in 70 grams of diethylene glycol and less than two hours to dissolve 200 grams of foam in 100 grams of diethylene glycol when the temperature of the liquid is maintained at about 190° C. The dissolution rate is faster at higher temperatures.

The amounts and rates will, of course, vary with other alcohols and depend on the particular foam used. Additionally, the size of the pieces of foam to be dissolved will affect the time required for dissolution. Generally, foam pieces of about 3"×3"×3" are conveniently used. However, various factors such as reactor size and type of foam will influence the optimum size of foam pieces to be processed according to this invention and both larger and smaller pieces may be used.

Following dissolution, water and an alkali metal hydroxide are added to the solution either separately or as a solution of catalyst in water. The water is added in an amount sufficient to produce a solution that would boil at a temperature of between about 175° C. and about 220° C. When using preferred diethylene glycol, water is added in an amount by weight of between about 2.4% and about 0.6% of the diethylene glycol, preferably in an amount of about 1.1% by weight to maintain the stated temperature. The catalyst is added in an amount of at least about 0.1, preferably from about 0.1 to about 10, weight percent based on the weight of the foam, with 0.5 to about 3 weight percent being more preferred, 1.5 weight percent being most preferred. Although any alkali metal hydroxide can be used as a catalyst, sodium hydroxide is preferred. It is relatively inexpensive and does not precipitate out of solution in the presence of carbon dioxide, a hydrolysis reaction by-product. Lithium hydroxide can also be used as a catalyst. However, in this instance, a compound such as calcium hydroxide preferably is added. The calcium hydroxide reacts with the carbon dioxide, leaving the lithium hydroxide in solution to function as a catalyst. Otherwise, the lithium hydroxide can react with the carbon dioxide and be removed from the solution as a precipitate. Calcium hydroxide would be added in an amount in excess of the lithium hydroxide, preferably in a weight ratio of about 10:1. If a compound such as calcium hydroxide is not added in addition to the lithium hydroxide, it will be necessary to continue adding lithium hydroxide to the solution, in order to maintain the desired concentration of lithium hydroxide catalyst.

However, since lithium hydroxide is relatively expensive, this is undesirable.

The solution containing water and catalyst may then be refluxed, using a reflux condenser 7 until substantially all the carbamates and ureas have been hydrolyzed to amines and alcohol. Since some of the water in solution is consumed during reaction, the desirable water concentration is maintained through the addition of small amounts of water during refluxing. By maintaining the concentration of water in solution, for example when using diethylene glycol, between about 0.6% and 2.4% as stated above, the temperature is correspondingly maintained between about 220° C. and 175° C. Other alcohols require different water concentrations. A temperature of 200° C., which for diethylene glycol corresponds to about 1.1% water, is preferred.

The completeness of the hydrolysis reaction is periodically determined by analyzing a sample of the solution for carbamate concentration. This may be done conveniently using high performance liquid chromatography. When using diethylene glycol hydrolysis is complete in less than 4 hours at the preferred concentrations of water and catalyst, most of the carbarmates having been hydrolyzed in about 30 minutes. The time required for hydrolysis appears to be independent of the particular foam to alcohol ratios used, as long as they are maintained within the limitations of this invention. However, the time may vary based on the particular alcohol, foam, temperature and catalyst including amount used, for example.

After hydrolysis is complete and prior to the addition of the alkane, any water present in solution must be removed. If this is not done, spattering will take place when the solution and the alkane are combined. The water can be simply removed by bypassing the condenser and heating the solution to about 220° C. for a short period of time in order to vaporize the water.

If the solution is allowed to stand, layer formation may occur. It appears dependent on the alcohol used and on the foam used. For example, when using the preferred alcohol, diethylene glycol and clean scrap foam, the solution separates into a polyol layer and a diethylene glycol layer, however, when using diethylene glycol and waste foam contaminated with oil, brake fluid and other manufacturing products, layer separation does not readily take place.

The extraction of the polyol begins with the addition to the solution, which may have separated into layers, of an alkane whose boiling point is between about 230° C. and 300° C. The alkane is added with stirring, preferably in an approximately equal amount by weight relative to the weight of the scrap foam. Since in the preferred embodiment of this invention, the foam to alcohol weight ratio is approximately 1:1, the preferred alcohol to alkane weight ratio would therefore by approximately 1:1.

Any paraffinic hydrocarbon may be used that has the required boiling point range and additionally is substantially immiscible with the alcohol used. Preferably, in this invention, hexadecane is used in combination with diethylene glycol. The alkane solvent may be a mixture of suitable alkanes and may also include isomeric forms of these hydrocarbons, for example, diesel fuel. The temperature of the solution, with continued stirring, is brought to between about 200° C. and 220° C. Thereafter, and while the temperature is maintained between about 200° C. and 220° C., stirring is discontinued and the solution readily separates into two layers. One layer comprises the alkane containing the polyol and the other layer comprises the alcohol. In the preferred use of diethylene glycol and hexadecane, the top layer comprises hexadecane-polyol and the lower layer comprises diethylene glycol.

After removing the alkane polyol layer, it is allowed to cool whereby it further separates into an alkane layer and a polyol layer. In one process of the invention wherein diethylene glycol, hexadecane and clean foam were used, layer separation took place at about 175° C. into an upper hexadecane layer and a lower polyol layer.

The polyol layer is then removed. Additionally, the remaining alkane layer can similarly be used to perform further extractions of polyol from the alcohol layer of the previous step, if desired, in order to recover additional polyol. Thus, in the preferred use of diethylene glycol and hexadecane, the still relatively hot hexadecane would be added to the retained diethylene glycol layer, heated to about 200° C. with stirring, and then allowed to stand, whereupon separation into the upper hexadecane-polyol and lower diethylene glycol layers would again take place. Subsequently, the upper layer would be removed and allowed to cool, preferably to about 175° C., whereby layer separation would take place. Thereafter the lower polyol layer would be removed. If dirty foam was used in the process of the invention, contaminents such as oil or brake fluid would dissolve in the alkane and thus be separated from the polyol.

All of the polyol recovered may then be subjected to vacuum purification at a temperature below about 230° C. in order to remove any amines, water, alcohol or alkane present. Vacuum purification as used in this application includes any process by which desirable end product (polyol) and impurities are separating using vacuum means. Exemplary of such means are conventional distillation apparatus and thin film evaporators. Other apparatus for effecting the desired separation will be apparent to those skilled in the art. Relatively pure polyol is recovered which can then be used to replace virgin polyol in new foam production.

Figure 2:
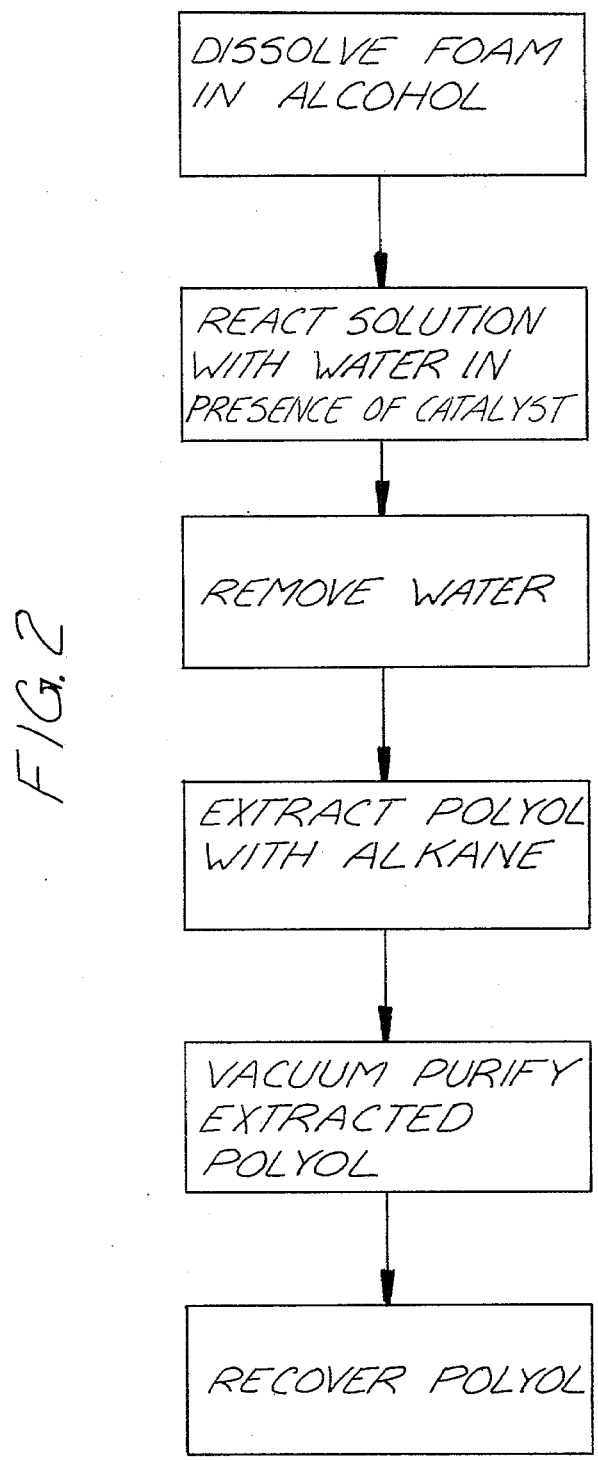
FIG. 2 is a flow diagram illustrating the subject process.
Figure 3:
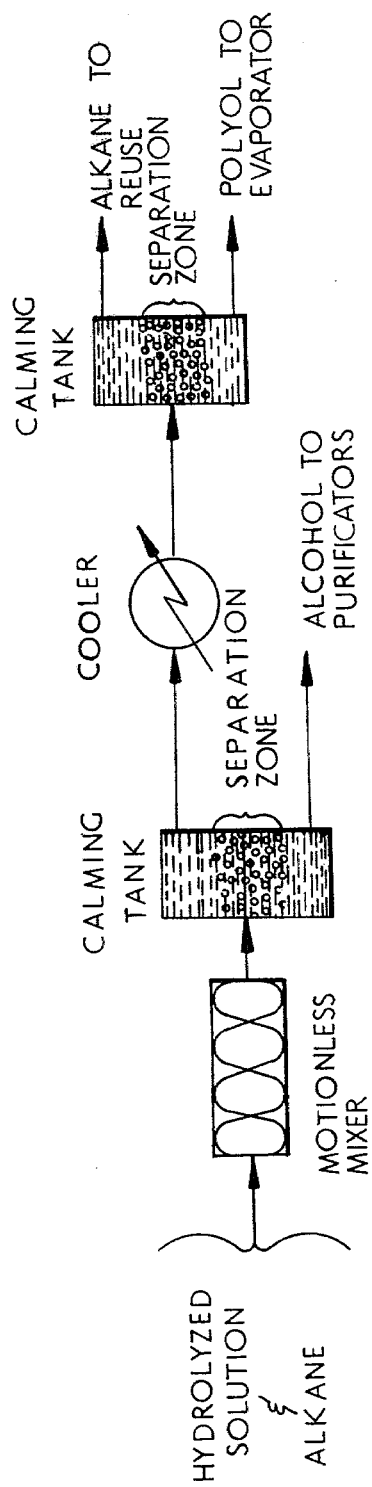
FIG. 3 schematically illustrates continuous process equipment which could be used to carry out the extraction step of the subject invention.

This process is illustrated schematically in the flow diagram shown in FIG. 2. FIG. 3 illustrates schematically continuous process equipment which could be used for extraction in this process. Using this equipment, the hydrolyzed solution and alkane mixture would be agitated in a static mixer, and therafter sent to a first calming tank where separation would take place into a polyol-alkane layer and an alcohol layer. The layers would then be separated. After removal, the alcohol layer would be subject to purification and the alkane-polyol layer would be cooled and thereafter sent to a second calming tank. Where it would separate into an alkane layer and a polyol layer. The alkane layer could, after separation, be reused for further extraction. The removed polyol is then subject to vacuum purification, such as by thin film evaporation.

The following examples are offered to show the method of operation of the process of this invention, but are not to be construed as limiting as to the process of this invention.

EXAMPLE 1

A random sample of polyurethane foam waste contaminated with oil, brake fluid, water, plastic metal, glass and rubber debris was gathered at an automobile shredder site. A 600 gram sample of this material was dissolved, as is, in an equal weight of diethylene glycol at 200° C. under a nitrogen atmosphere in 100 grams increments over a 1 hour period with rapid stirring. A black viscous particulate ladden mixture was obtained. The reaction vessel was fitted with a reflux condenser and 6 grams of sodium hydroxide and 6 grams of water were added. The mixture was allowed to reflux at 200° C. with stirring for two hours, cooled and then split into two fractions for additional treatment. A 600 gram fraction of the reaction mixture above was heated to 225° C. to drive off water and mixed with 300 grams of technical grade hexadecane. When the temperature of the mixture was brought back to 195° C. and stirring discontinued, two distinct layers rapidly separated in the reactor. The upper layer was light brown in color while the lower layer was a black and turbid. The upper layer was removed and allowed to cool in a separating funnel. When the mixture had cooled to 150° C., phase separation occurred to yield to a dark upper layer, identified by infra-red spectroscopy and high performance liquid chromatography to contain mostly hexadecane and motor oils, and a clear tight amber lower layer containing mostly polyether triols of polypropylene oxide with about 10% by weight diethylene glycol, about 6% by weight hexadecane and 3% by weight toluenediamines. Vacuum purification of the lower layer at a pressure of 2 mm of mercury and 195° C. in a thin film evaporator produced 175 grams of essentially pure polyol with molecular weight distribution, infrared spectrum and hydroxyl number virtually indistinguishable from commercially available Pluracol 535 polyol.

The polyol produced was used to replace 10% by weight of the Pluracol 535 in the polyurethane foam formulation given in Table 1. A flexible, high resiliency foam with a density of 2.3 pounds per cubic foot was produced.

Table I
FORMULATION OF FLEXIBLE POLYURETHANE FOAM

| Material | Parts by | Description |
|---|---|---|
| 1. Pluracol 535 (Polyol) (BASF) | 75 | 1640 eq. wt. mostly triol |
| 2. Pluracol 581 (Polyol) (BASF) | 25 | 2078 eq. wt. mostly triol; contains styrene and acrylonitrile |
| 3. Water | 2.8 | Distilled |
| 4. DABCO (Air Prod.) | 0.14 | Triethylene diamine |
| 5. X-DM (Air Prod.) | 0.20 | Dimethylaminoethylmorpholine |
| 6. A-1 (Union Carbide) | 0.10 | 70% bis(2-Dimethylaminoethyl) ether, 30% dipropylene glycol |
| 7. Q-1-5043 (Dow Corning) | 1.4 | Silicone glycol copolymer surfactants |
| 8. T-12 (M & T) | 0.015 | Dibutyl Tin Dilaurate |
| 9. E-422 (Mobay) | 35.78 | Polymeric Isocyanates, 20% MDI, 80% TDI |

EXAMPLE 2

The second sample of the immediate dissolution and hydrolysis mixture prepared in Example 1 was allowed to stand without heating whereupon it could cool to 150° C. in a nitrogen atmosphere. The mixture separated slowly into two very dark layers. The upper layer was analyzed by high performance liquid chromatography and gel permeation chromatography and shown to be rich in polyether triol, diethylene glycol and a large number of unidentified components. This material was subjected to thin film vacuum distillation at 2 mm of mercury and 195° C. to obtain a viscous, dark product. Low density polyurethane foam could not be produced when this product was substituted at the 10, 5, and 3 percent by weight levels for Pluracol 535 in the formulation given in Table 1. A coarse, low density foam weighing 2 pounds per cubic foot was produced when Pluracol 535 was replaced at the 1.5% level. The cell structure of this foam was very uneven. A good low density foam could be produced at a 1% Pluracol 535 substitution level.

EXAMPLE 3

A 600 gram sample of waste industrial polyurethane foam prepared according to the formulation given in Table 1 was processed following the procedure described in Example 1. 165 grams of polyol were recovered from the hexadecane processed fraction. The recovered polyol was used to replace 50% by weight of the Pluracol 535 in the formulation of Table 1. A high resiliency flexible polyurethane foam with density of 2.12 pounds per cubic foot was produced indicating that the recovered polyol is comparable in usefullness to virgin polyol.

EXAMPLE 4

The second sample of the dissolution and hydrolysis mixture prepared in Example 3 was allowed to stand without heating whereupon it could cool to 150° C. in a nitrogen atmosphere. The mixture separated slowly into two layers, a light brown upper layer containing mostly polyols and a lower layer containing mostly diethylene glycol. After vacuum distillation of the polyol layer at 2 mm of mercury and 195° C., the polyol residuum was used to replace 50, 25, 15, 10, 5 and 2 percent by weight of the Pluracol 535 in the formulation given in Table 1. At 50 and 25 percent replacement, the polyurethane foam collapsed during the reaction giving a tough, dense rubbery product. At 15 percent replacement, a coarse low density foam was produced. At 10 percent or less replacement, good quality low density polyurethane foams were produced. Thus, hexadecane extraction as in Example 3 produces a substantially higher quality polyol.

EXAMPLE 5

The procedure described in Examples 3 and 4 is repeated, except 600 grams of glycerol are used instead of diethylene glycol. In addition 13.5 grams of water are used to maintain the reflux temperature during hydrolysis. The polyols produced with hexadecane extraction again can be used to replace 50 percent by weight of the Pluracol 535 in the formulation of Table 1 and produce good low density foam. The polyol produced without hexadecane extraction produces good low density foam at a replacement level of only 8 percent.

EXAMPLE 6

The procedure of Examples 3 and 4 is repeated using a diesel fuel cut with boiling range of 250° C. to 295° C. instead of hexadecane. Results obtained are similar to the results described in Examples 3 and 4.

In view of this disclosure, many modifications of this invention will be apparent to those skilled in the art. It is intended that all such modifications which fall within the true scope of the invention will be included within the terms of the appended claims.

What is claimed is:

1. A process for recovery of substantially pure polyether polyol from polyether polyurethane foam which can be used to make high quality new foam, comprising the steps of:
    (a) forming a solution by dissolving said polyether polyurethane foam in a saturated alcohol having a boiling point of between about 225° C. and about 280° C. at a temperature between about 185° C. and about 220° C. under a non-oxidizing atmosphere;
    (b) refluxing said solution under said non-oxidizing atmosphere in the presence of an alkali metal hydroxide catalyst and water, said water being included in said solution in an amount sufficient to create a mixture which has a boiling point within the temperature range of from about 175° C. to about 220° C., for a time necessary to substantially hydrolyze dissolution products subject to hydrolysis into amines and alcohol while (1) periodically adding a sufficient amount of water to maintain a mixture having a boiling point within said range of from about 175° C. to about 220° C. and (2) maintaining said solution at a temperature in said range, and wherein said alkali metal hydroxide catalyst is included in said solution in an amount of at least 0.1 weight percent based on the weight of said polyurethane foam;
    (c) removing water remaining after hydrolysis from said solution under a non-oxidizing atmosphere;
    (d) extracting said polyol from the hydrolyzed solution under a non-oxidizing atmosphere with an alkane substantially immiscible with said alcohol and having a boiling point between about 230° C. and about 300° C.; and
    (e) subjecting the extracted polyol to vacuum purification at a temperature below about 230° C. so as to allow recovery therefrom of substantially pure polyether polyol.

2. A process according to claim 1, wherein said extracting step comprises the steps of:
    (a) adding to said hydrolyzed solution said alkane with mixing while heating to a temperature of between about 200° C. and about 220° C.
    (b) discontinuing mixing while maintaining the temperature between about 200° C.–220° C., whereby said mixture separates into a layer comprising said alkane-polyol mixture and a layer comprising said alcohol;
    (c) removing said alkane-polyol mixture layer;
    (d) cooling said alkane-polyol mixture to effect separation into a layer comprising said alkane and a layer comprising said polyol; and
    (e) removing said polyol layer.

3. A process according to claim 1 or 2, wherein the weight ratio of said foam to said alcohol is between 1:5 and 2:1.

4. A process according to claim 1 or 2, wherein said weight ratio of said foam to said alcohol is preferably 1:1.

5. A process according to claim 1 or 2, wherein said alcohol is a diol or triol containing an ether linkage.

6. A process according to claim 5, wherein said alcohol comprises dipropylene glycol, dibutylene glycol or diethylene propylene glycol.

7. A process according to claim 6, wherein said alcohol is diethylene glycol.

8. A process according to claim 7, wherein said water is present in solution during hydrolysis in an amount by weight based on weight of said diethylene glycol of between about 2.4% and 0.6%.

9. A process according to claim 1 or 2, wherein the temperature of said solution during dissolution step (a) is about 200° C.

10. A process according to claim 1 or 2, wherein said alkali metal hydroxide in said solution during hydrolysis in an amount of between about 0.1 and about 10 weight percent based on said polyurethane foam.

11. A process according to claim 10, wherein said catalyst is included in said solution during hydrolysis in an amount of between about 0.5 and about 3 weight percent based on said polyurethane foam.

12. A process according to claim 11, wherein said catalyst is included in said solution during hydrolysis in an amount of about 1.5 weight percent based on said polyurethane foam.

13. A process according to claim 1 or 2, wherein said alkali metal hydroxide catalyst is sodium hydroxide.

14. A process according to claim 1 or 2, wherein said catalyst is lithium hydroxide.

15. A process according to claim 14, wherein the process further comprises adding calcium hydroxide in a weight ratio of about 10:1 relative to the lithium hydroxide.

16. A process according to claim 1 or 2, wherein weight ratio of said alkane to said alcohol is about 1:1.

17. A process according to claim 1 or 2, wherein said alkane is a mixture of alkanes.

18. A process according to claim 1 or 2, wherein said alkane is technical grade hexadecane.

19. A process according to claim 1 or 2, wherein step of removing said water from said solution after hydrolysis comprises heating said solution to about 220° C. to vaporize said water from said solution.

20. A process according to claim 1 or 2, wherein said vacuum purification comprises thin film vacuum evaporation.

21. A process according to claim 1 or 2, wherein said vacuum purification comprises batch vacuum purification.

22. A process according to claim 1 or 2, wherein said non-oxidizing atmosphere comprises nitrogen.

23. A process according to claim 2, wherein said alkane layer remaining after removal of said polyol layer is reused for further polyol extraction.

24. A process according to claim 1, wherein dissolving said polyurethane foam in said alcohol (a) causes dissolution of said polyurethane foam into dissolution products comprising polyol, carbamates and ureas, wherein said carbamates and ureas are subject to hydrolysis into amines and alcohol during step (b).

25. A process recovery of substantially pure polyether polyol from polyether polyurethane foam which can be used to make high quality new foam, comprising the steps of:
    (a) forming a solution by dissolving said polyether polyurethane foam in diethylene glycol at a temperature between about 185° C. and about 220° C. under a nitrogen atmosphere;
    (b) refluxing said solution under nitrogen in the presence of sodium hydroxide catalyst and water for a time necessary to substantially hydrolyze dissolution products subject to hydrolysis into amines and alcohols while (1) periodically adding water to maintain the weight percent thereof in relationship to said diethylene glycol in the range of between about 0.6% and 2.4% and (2) maintaining said solution temperature between about 175° C. and 220° C., wherein said water is included in an amount by weight of between about 2.4% and 0.6% based on the weight of said diethylene glycol and the sodium hydroxide is included in said solution in an amount by weight of between about 0.1% and 10% based on the weight of said polyurethane foam;

(c) removing water remaining in said solution after hydrolysis under a nitrogen atmosphere;

(d) extracting said polyol from the hydrolyzed solution under a nitrogen atmosphere with hexadecane; and (e) subjecting the extracted polyol to vacuum purification at a temperature below about 230° C. so as to allow recovery therefrom of substantially pure polyether polyol.

* * * * *